United States Patent [19]
Carl

[11] Patent Number: 6,102,984
[45] Date of Patent: Aug. 15, 2000

[54] APPARATUS FOR MOVING FLUIDS BETWEEN MICROPLATES UTILIZING TWO PLATE TRANSPORT MECHANISMS

[75] Inventor: Richard A. Carl, Rancho Palos Verdes, Calif.

[73] Assignee: Packard Bioscience Company, Meridan, Conn.

[21] Appl. No.: 09/188,450

[22] Filed: Nov. 9, 1998

[51] Int. Cl.⁷ ........................................ G01N 1/00
[52] U.S. Cl. ........................................ 75/866.24
[58] Field of Search ............ 73/864.17, 864.23, 73/864.24, 864.25, 863.32; 436/43, 48, 180, 804; 422/63, 100, 102

[56] References Cited

U.S. PATENT DOCUMENTS

| | | |
|---|---|---|
| 3,687,632 | 8/1972 | Natelson ........................... 73/864.25 |
| 4,812,392 | 3/1989 | Miyake et al. . |
| 4,841,786 | 6/1989 | Schulz ................................. 73/864.25 |
| 5,055,263 | 10/1991 | Meltzer ............................... 73/864.25 |
| 5,306,510 | 4/1994 | Meltzer ............................... 73/864.24 |

*Primary Examiner*—Robert Raevis
*Attorney, Agent, or Firm*—Irving Keschner

[57] ABSTRACT

Apparatus for transferring liquid from a first microplate having x wells to a second microplate having y wells. A dispense head aspirates fluid from the first microplate and then dispenses fluid into the y wells corresponding to the wells from the first microplate by moving the second microplate in a predetermined sequence. Preferably, dual air cylinders are used to move the microplate and are operatively coupled to first and second motion plates to provide the proper dispensing movement sequence. X may be less than, greater or equal to Y.

11 Claims, 5 Drawing Sheets

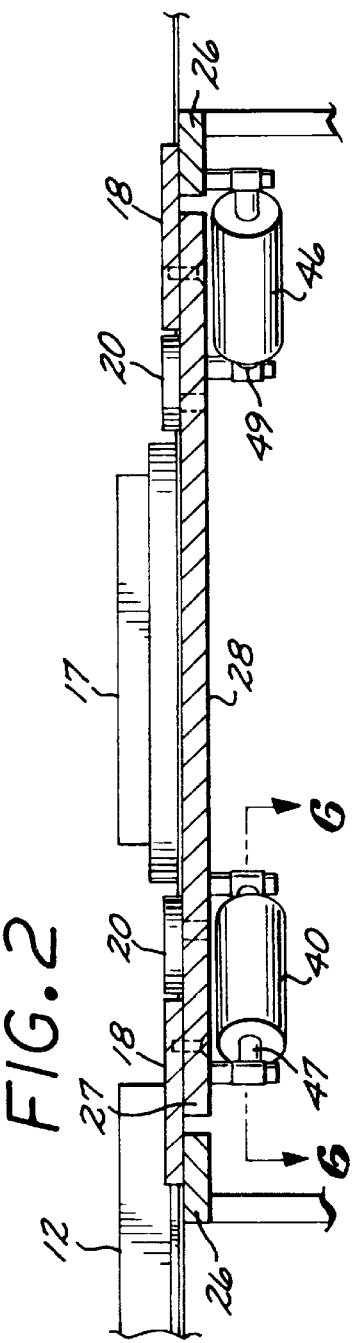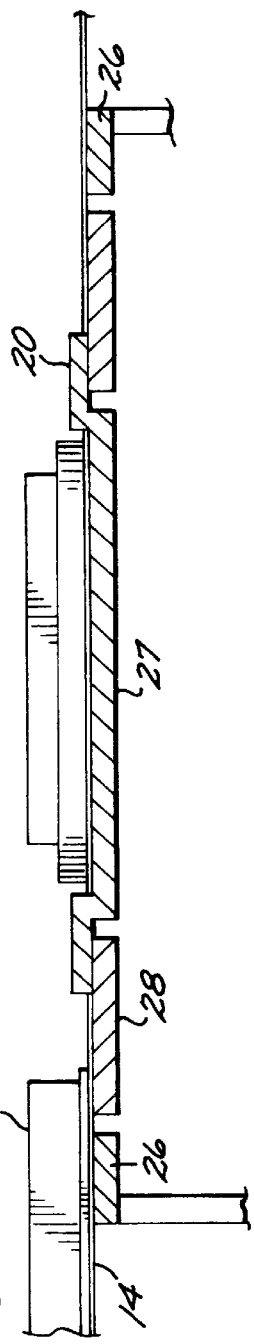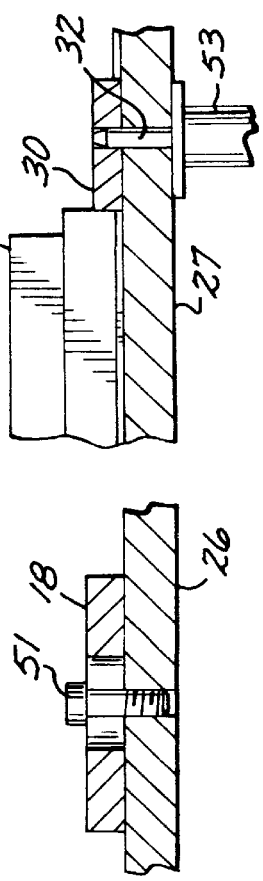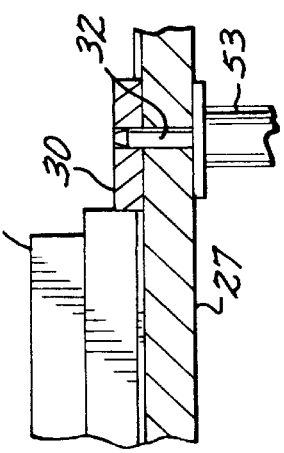

| RESULT POSITION | CYL.1 EXTENDED | CYL.1 RETRACTED | CYL.2 EXTENDED | CYL.2 RETRACTED | DISTANCE CHANGE |
|---|---|---|---|---|---|
| POSITION 1 |  | X |  | X | 0 |
| POSITION 2 |  | X | X |  | .1263 |
| POSITION 3 | X |  |  | X | .2506 |

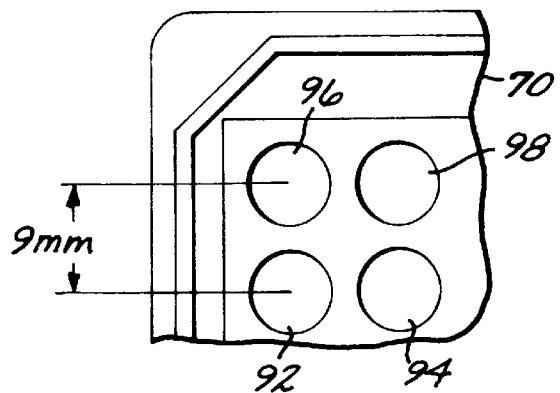
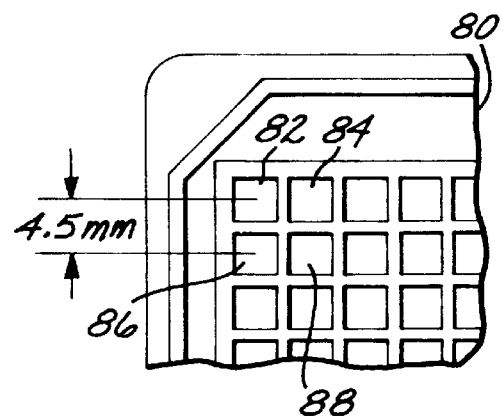
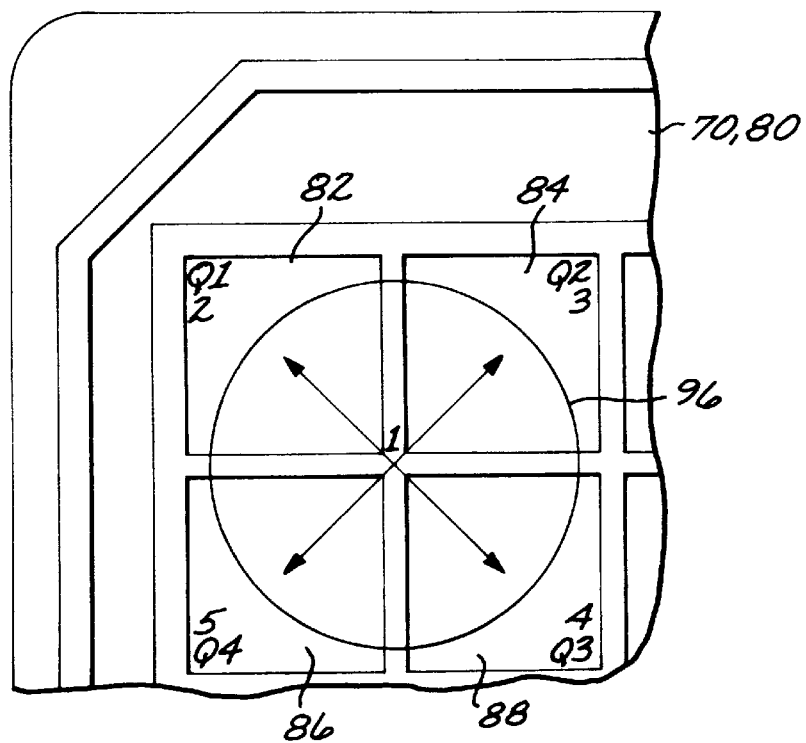

APPARATUS FOR MOVING FLUIDS BETWEEN MICROPLATES UTILIZING TWO PLATE TRANSPORT MECHANISMS

BACKGROUND OF THE INVENTION

1. Field of the Invention

The present invention provides apparatus for moving a microplate to accommodate higher density microplates when fluid is being dispensed from a conventional 96 head pipette dispenser.

2. Description of the Prior Act

U.S. Pat. No. 5,497,670 issued Mar. 12, 1996, the subject matter set forth therein invented by the inventor of the present invention, discloses an improved dispensing head apparatus including means for loading pipette tips carried by a pipette plate onto liquid dispensing cylinders, the loading force being maintained during the apparatus operation cycle, thus ensuring a proper seal between the pipette tip and the cylinder. The pipette tips are manually placed on the tip plate, the plate sliding within the dispensing apparatus.

Although the pipette tip plate holder described in the aforementioned patent provides many advantages when used with the apparatus described therein, there are certain disadvantages associated with it use. In particular, there is a possibility that the pipette tip plate holder may become contaminated. More importantly, the pipette tip plate configuration is not easily adapted for robotics operation or automation.

U.S. patent application Ser. No. 08/751,859 filed Nov. 18, 1996 the subject matter set forth therein also invented by the inventor of the present invention, provides a self contained fluid head dispensing apparatus similar to that disclosed in the aforementioned patent but modified to the extent that the pipette tip plate disclosed therein is replaced with a more conventional pipette tip box which is less expensive, is less likely to be contaminated and wherein the carrier is easily adapted for robotics operation or automation.

A microplate containing 96 wells with 9 mm on centers spacing in a 8 by 12 array is typically used with most dispense apparatus. The early prior act dispense devices started with one fluid dispenser and moved in the x-y direction 96 times to dispense into each of the 96 wells. Over time, dispense devices were added to include one row (8 or 12 wells per row) and then indexing either 8 or 12 times to fill the entire plate. A 96 dispense apparatus device to fill an entire plate at one time is disclosed, for example, in the '670 patent noted above.

The microplate has recently changed in design. Higher production speeds and larger storage libraries require higher density formats. The 96 well format with its 9 mm spacing has increased to 384 wells with 4.5 mm spacing. The 384 microplate has increased to 864 and now 1536 with 2.25 mm spacing between well centers. These different density plates have the same foot print (length, width).

A 96 head pipette dispenser can be used for either 96 well plates or higher 384 or 1536 density well plates. Therefore, there is a need to either move the dispense head or the plate for the higher density plates. Since it is easier to move the microplate rather than move the relatively heavy dispense head, it is an obvious choice to design a system to move the microplate. The 96 head pipette dispenser can work with a 384 well microplate if the head or microplate is moved 4 times and dispensed 4 times (FIG. 7 to FIG. 8). Therefore a 96 pipette dispense head can move fluid from one 384 plate to another 384 plate, the wells being designated as quadrant in a four well configuration. This is accomplished in a quadrant to quadrant move (one well being designated as a quadrant). In the first move, fluid from a first well of the first plate is moved to the first well of the second plate. Therefore, there are 4 moves required for a 384 to 384 transfer.

There is frequently a need to preform a conversion from 96 to 384 well formatted plates (compression) or 384 to 96 well formatted plates (expansion). If 96 to 384 conversion is needed, it will require 5 motions, one aspirate and four dispenses. Thus what is desired is to provide a 5 position motion device which enables fluid to be accurately transferred between 384 and 96 well formatted plates and other well formatted plates (i.e. from a 384 well formatted plate to a 1536 well formatted plate).

SUMMARY OF THE PRESENT INVENTION

The present invention provides a device which enables the accurate transfer of fluid between 96 and 384 (and higher) microplates, the device providing 5 motion positions for the microplate. One method of moving the plate is to use small motors (servo, stepper, etc.) and move the plate in a bi-directional motion using "X" and "Y" axis motors. Motors, although flexible, are costly and require support hardware and control electronics.

The present invention utilizes four dual air cylinders (the dual air cylinders comprise back to back conventional air cylinders) to provide the desired 5 position motion to move fluid from a 96 pipette dispense head into a 384 well microplate, or a 384 pipette dispense head into a 1536 well microplate. Both require only 5 motions but the total cylinder stroke length is different. For the 96 to 384 motion, the stroke length is 0.1253 inches; for the 384 to 1536 conversion, the stroke length is 0.0628 inches. Other conversions have proportional stroke lengths.

The microplate into which fluid is being transferred is moved to a transfer station having a fixed plate and two movable plates. Two dual air cylinders are connected to diagonally opposite corners of the first and second movable plates and controlled in a manner to provide the 5 positions required.

DESCRIPTION OF THE DRAWING

For a better understanding of the invention as well as other objects and further features thereof, reference is made to the following description which is to be read in conjunction with the accompanying drawing wherein:

FIG. 2 is a cross sectional view along line 2—2 of FIG. 1 showing the first movable plate;

FIG. 3 is cross sectional view along line 3—3 of FIG. 1 showing the second movable plate;

FIG. 4 is a cross sectional view along line 4—4 of FIG. 1 showing a slot which causes the microplate to move in a desired direction;

FIG. 5 is cross sectional view along line 5—5 of FIG. 1 showing the air cylinder pistons extended to stop the microplate forward motion and maintain the position of the plates during the quadrant move on the plate transfer station;

FIG. 7 illustrates a 96 well microplate;

FIG. 8 illustrates a 384 well microplate;

FIG. 9 shows the 384 well microplate overlaid with the 96 well microplate and the required plate movement.

DESCRIPTION OF THE INVENTION

Figure 10:
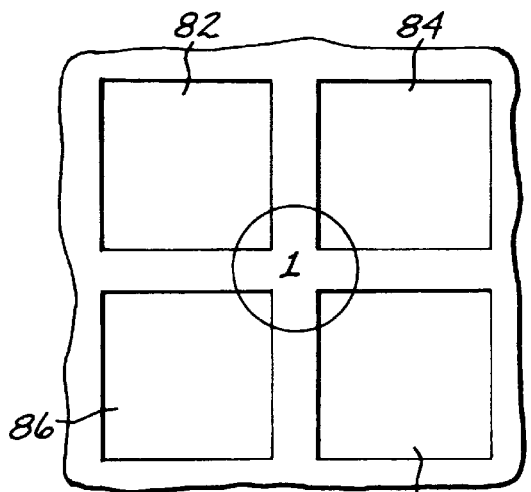
FIG. 10 through 15 illustrates typical movements of the motion plate for proper dispensing of fluid from the dispense head apparatus.
Figure 11:
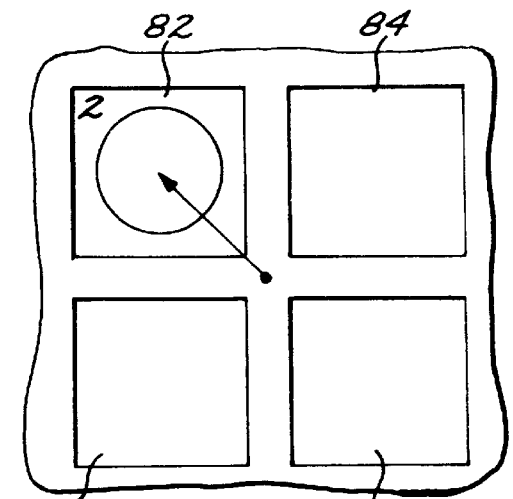

Referring first to FIG. 7, a portion of a 96 well microplate 70 having circular shaped wells 92, 94, 96 and 98 is illustrated, the spacing between centers of each well being approximately 9 millimeters. FIG. 8 illustrates a portion of a 384 well microplate 80, having square shaped wells 82, 84, 86, 88 and so on, the spacing between well centers being approximately 4.5 millimeters. If fluid is contained in the 96 well plate 70 (FIG. 7) and is to be moved to 384 well plate 80, the first dispense/aspirate cycle will start at position 1 (FIG. 9 shows a portion of the 96 well microplate overlying a portion of the 384 well microplate) to illustrate how a single well 96 of the 96 well microplate 70 corresponds to four wells 82, 84, 86 and 88 of 384 well microplate 80, and then to position 2. The cycle will continue and require 5 motions. FIGS. 10–15 illustrate the microplate movement provided by the apparatus shown in FIGS. 1–6. The motion always starts from center position 1 as shown in FIG. 10 and radiates to the desired quadrant or well.

Figure 12:
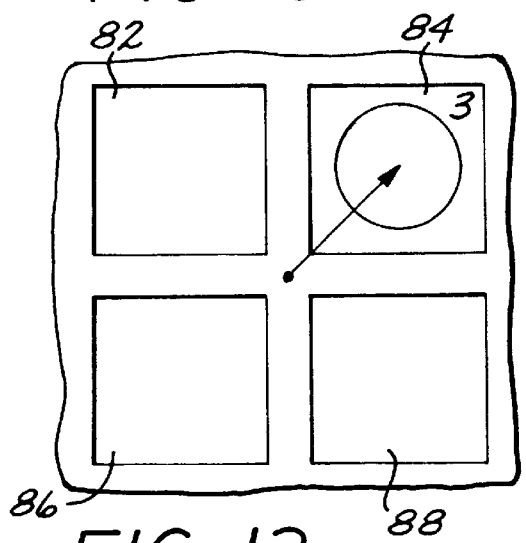
Figure 13:
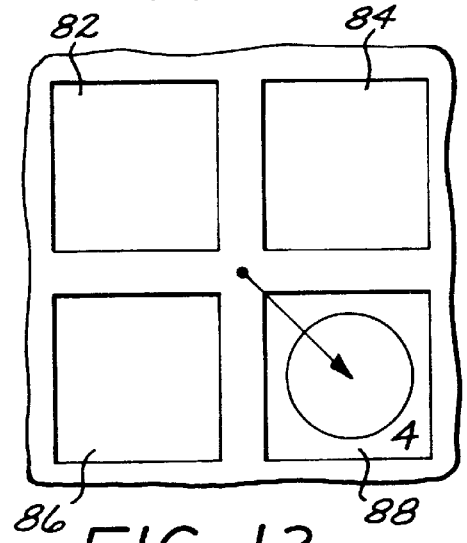
Figure 14:
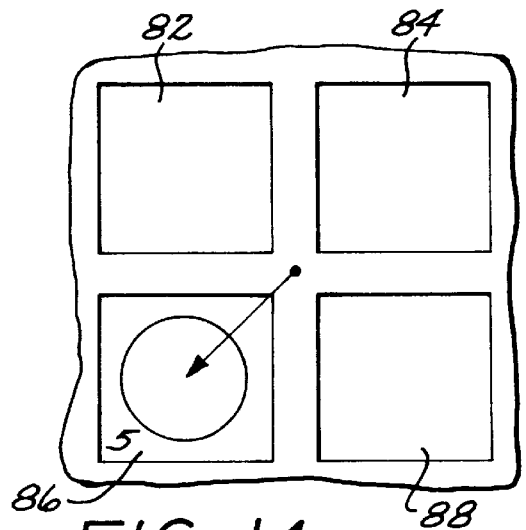
Figure 15:
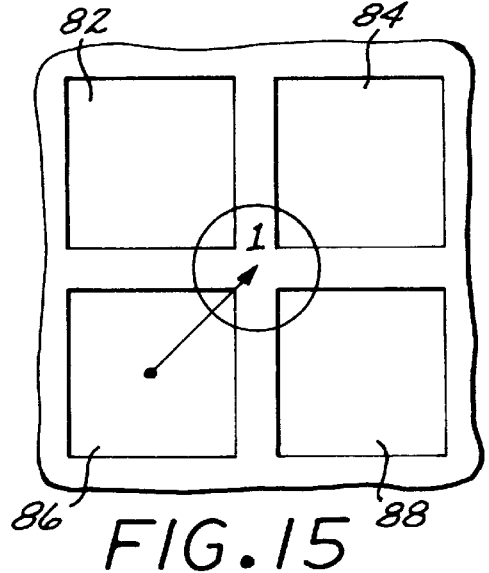

In the process described hereinafter, fluid is to be transferred from a 96 well microplate to a 384 well microplate. In this case, a first set of dual air cylinders (described hereinafter) moves microplate 80 in a diagonal motion from center point 1 (FIG. 10) to quadrant 2 (corresponding to well 82) shown in FIG. 11. The plate 80 is then moved back to center position 1 as shown in FIG. 10. The second set of dual air cylinders then moves microplate 80 from center point 1 to quadrant 3 (corresponding to well 84) as shown in FIG. 12. The first set of dual air cylinders then moves microplate 80 from center point 1 (FIG. 10) to quadrant 4 (corresponding to well 88) as shown in FIG. 13 and then returns to center position 1. The first set of dual air cylinders then moves microplate 80 from center position 1 to quadrant 5 (corresponding to well 86) as shown in FIG. 14 and then back to center point 1 as shown in FIG. 15.

When one set of dual air cylinders are operative, the pistons of the other set of dual air cylinders are positioned so that movement of microplate 80 starts from center point 1.

Figure 1:
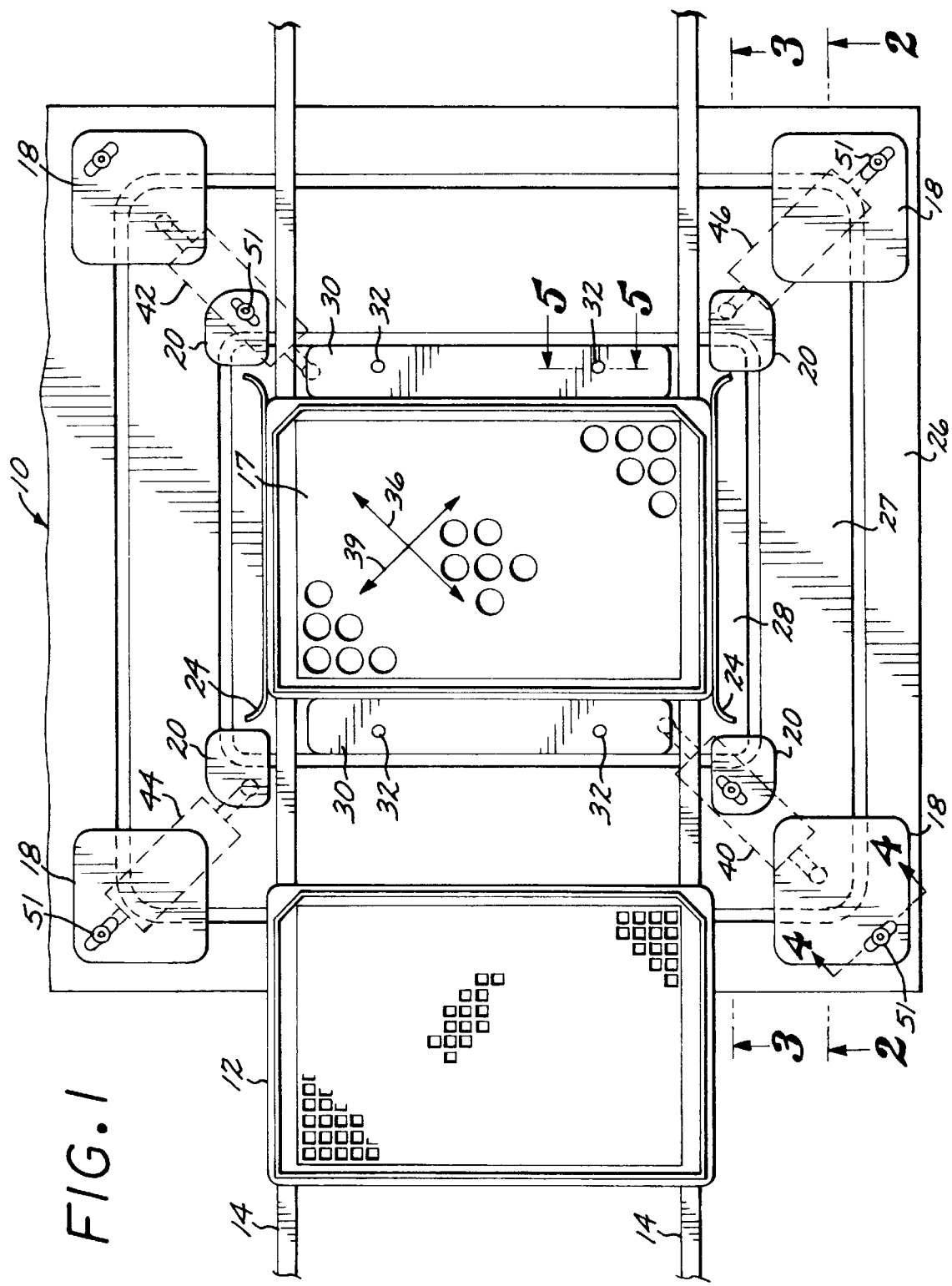
FIG. 1 is a top plan view of the motion plate apparatus of the present invention.

Referring now to FIG. 1, the device 10 of the present invention for moving microplates with respect to a dispense head apparatus (not shown) to transfer fluid from one microplate having a predetermined number of wells to another microplate having a different number of wells. In the apparatus illustrated, 384 well plate 12 is shown being transported along conveyor belts 14 to station 16 to replace 96 well microplate 17 as it is transported out of the station 16 after liquid has been aspirated therefrom.

Device 10 comprises slide bearing pads 18, slide bearing members 20, tray guides 24, fixed plate, or table 26, first movable plate 27, second movable plate 28, tray stops, or bars, 30 having rods 32 extending through holes formed therein, four dual air cylinders 40, 42, 44 and 46 arranged in pairs or groups (the first pair comprising dual air cylinders 40 and 42, the second pair comprising dual air cylinders 44 and 46), the first pair being mounted to first movable plate 27 and the second pair mounted to second movable plate 28 so that microplate 12 can be moved to five positions to accommodate the transfer from 96 well microplate 17 to 384 well microplate 12.

Tray, or microplate, motion is achieved by using motion plates 27 and 28 and fixed plate 26. The two motion plates are connected to four slide bearing plates located at their four corners. In particular, motion plate 27 has four sliding bearing pads 18 mounted on the outside four corners and second motion plate 28 has four slide bearings 20 mounted on the outside four corners. Motion plate 27 is supported by the four slide bearings 18, slide bearings 18 resting on fixed plate 26. In a similar motion, plate 28 is supported on its outside four corners by slide bearings 20, plate 28 and slide bearings 20 rest on slide plate 27. The slide bearing pads ride on top on the adjacent motion plate, each motion plate being slotted with a bearing passing thought it. These slots enable the first and second motion plates 27 and 28, respectively, to move in the correct plane (45° to 135°) with reference to point 1 (FIG. 10). Dual air cylinders 40 and 42 are connected to two of the four corners of slide motion plate 27 and dual air cylinders 44 and 46 are connected to two of the four corners of slide motion plate 28 as illustrated. Each of the dual air cylinders are connected together, one pushing and the other one pulling when energized, allowing the motion, or slide plates, 27 and 28 to move in a fixed direction at 45° and 135°. The conveyor belt 14 moves the microplate 12 into the center most slide plate 28, where it is held by tray stops 30 on each side. Conveyor belt 14 allows the microplate 12 to move into the station 16 and can be bi-directional, moving plates into and out of the station from either direction. Tray stops 30 have a dual function, they stop the microplate bi-directional movement relative to the conveyor belt and capture the microplate when the slide plates 27 and 28 move the microplate tray, keeping the microplate in position.

Referring now to FIGS. 1–5, the operation of device 10 is as follows:

Tray, or microplate, 12 is transported by belts 14 and is guided into place by tray guides 24. Microplate 12 is then stopped and locked into place by stops, or bars, 30. The guides 24 are fixed to first movable plate 28, the bars 30 being coupled to plate 28 by two air cylinder pistons that are connected to member 30. Plate 28 is supported on its four corners by bearing pads, or blocks, 20, the pads resting on movable plate 27. Plate 27 is supported on its four corners by bearing pads, or blocks, 18, blocks 18 resting on fixed table 26. As will be set forth in more detail hereinafter, cylinders 40, 42, 44 and 46 cause plates 27 and 28 to move, cylinders 40 and 42 moving plate 28 in the direction of arrow 36 only; cylinders 44 and 46 move plate 27 only in the direction of arrow 39, the directions being perpendicular to each other. Cylinders 40 and 42 are fixed between plates 27 and 28 and cylinders 44 and 46 are fixed between plate 28 and table 26.

As illustrated in FIG. 2, clevis 47 of air cylinder 40 (and cylinder 42, not shown) is coupled to movable plate 27 to provide the appropriate diagonal movement to microplate 12 when energized; clevis 49 of air cylinder 46 (and cylinder 44, not shown) is coupled to movable plate 28 to provide the appropriate diagonal movement to microplate 12 when energized.

The plates 27 and 28 are held in place by bolts 51 mounted in slots in the pads 18 and 20 as illustrated. Air cylinders are provided (only one air cylinder 53 is shown in FIG. 5 although four are utilized) so that the cylinder arms (arm 32 of cylinder 53 is illustrated) when extended, will stop the microplate forward motion and maintain the position of the plate during quadrant movement on the plate transfer station.

Figure 6:
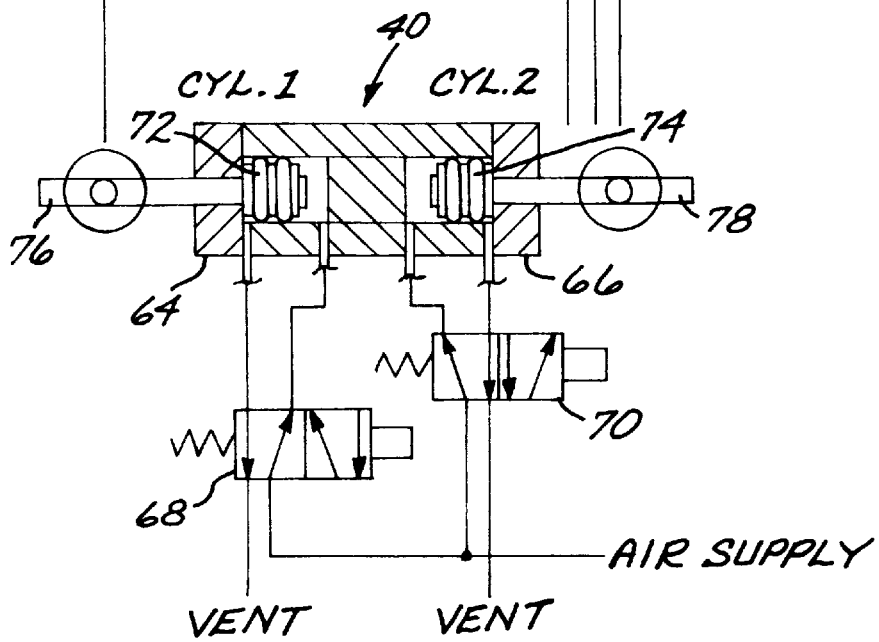
FIG. 6 is a cross-sectional view along line 6—6 of FIG. 2 illustrating the details of the dual air cylinder of the present invention.

FIG. 6 shows the dual air cylinder 40 in accordance with the teachings of the invention (since in cylinders 40, 42, 44 and 46 are identical, only the configuration and function of cylinder 40 will be described hereinafter). Cylinder 40 comprises separate cylinders 64 and 66 joined in a back to back arrangement. Valves 68 and 70 are provided to control the venting and air supply to the cylinders in a manner such that pistons 72 and 74 and their associated shafts, or clevis, 76 and 78, are capable of moving to three positions.

Specifically, the motion that is required to move motion plates 27 and 28 are provided by air cylinder 40, 42, 44 and 46, air cylinders 40 and 42 moving plate 27 and air cylinders 44 and 46 moving plate 28. Air cylinder 40 is actually two cylinders that are connected back to back, valves 68 and 70 moving each section of the air cylinder. Depending on which valve is energized (the valve control system, not shown, is conventional) and the position of the valves determine the position of the shaft portion of the cylinder. In essence, there are three positions that can be selected by the valves. It should be noted that one shaft of each dual air cylinder (shaft 76 of cylinder 40) is connected to a movable plate (plate 27 for cylinder 40) and the other shaft of each dual air cylinder (shaft 78 of cylinder 40) is connected to fixed plate 26.

The table at the top portion of FIG. 6 is set forth to illustrate the distance associated with the movements of rods 76 and 78 of dual air cylinder 40 (the example is for transferring fluid from a 96 well microplate to a 384 well microplate). In essence, the rods have three linear positions: position 1, no movement when both cylinder rods are retracted; (Position 2) movement of 0.1263 inches when rods 76 and 78 are extended (this last motion is not required since the 0.1263 inch movement is only necessary for the 96 to 384 conversion).

As shown in FIG. 1, if dual air cylinders 40 and 42 are mounted 45° to position number 1 (FIG. 9) and is moved as described hereinabove, motion to Q5 and to Q2 is achieved. It should be noted that one dual air cylinder pair can achieve three of the five required positions; if a second dual cylinder pair (44 and 46) is aligned at 90° to the first, as illustrated, an additional three more positions are achieved. Since position number 1 is common to both air cylinders, the result is essentially five possible positions.

What is claimed:

1. Apparatus for transferring fluid from a microplate having x wells to a microplate having y wells comprising:

a dispense head for aspirating fluid from the x well microplate;

means for transporting said y well microplate to a station in operative relationship to said dispense head; and pneumatic actuator means for moving said y well microplate in a manner such that the fluid from the x well microplate is transferred to the wells in the y microplate.

2. The apparatus of claim 1 wherein said pneumatic actuator means comprise a plurality of pneumatic actuators.

3. The apparatus of claim 2 wherein said plurality of pneumatic actuators each comprise dual air cylinders.

4. The apparatus of claim 3 whereas each of said dual air cylinders comprise two back to back air cylinders, each air cylinder comprising a piston and associated shaft, a valve and air supply means for controlling the position of said shafts.

5. The apparatus of claim 4 further including first and second motions plates and means for fixedly positioning said y well microplate with respect to said dispense head.

6. The apparatus of claim 5 wherein first and second dual air cylinders are connected to said first motion plate in a diagonal relationship.

7. The apparatus of claim 6 wherein third and fourth dual air cylinders are connected to said second motion plate in a diagonal relationship.

8. Apparatus for transferring fluid between microplates comprising:

a conveyor system for moving microplates in a first direction;

a fluid dispense station positioned approximately at the midpoint between the ends of said conveyor system, said fluid dispense station comprising a dispense head and means for securing a first microplate on a first motion plate beneath said dispense head; and pneumatic means for moving said first motion plate such that said first microplate is in alignment with said dispense head, said dispense head being adapted to aspirate, store, and dispense fluid from and to said first microplate.

9. The apparatus of claim 8 further including a second motion plate operatively coupled to said first motion plate.

10. The apparatus of claim 9 wherein said second motion plate is controlled by pneumatic actuator means.

11. The apparatus of claim 10 wherein said pneumatic actuator means each comprise dual air cylinders.

* * * * *